United States Patent
Stagg et al.

(10) Patent No.: US 9,651,680 B2
(45) Date of Patent: May 16, 2017

(54) GAMMA RAY SPECTROSCOPY MONITORING METHOD AND APPARATUS

(71) Applicant: Babcock & Wilcox Technical Services Group, Inc., Lynchburg, VA (US)

(72) Inventors: William R Stagg, Southern Pines, NC (US); Timothy A Policke, Forest, VA (US)

(73) Assignee: BWXT Technical Services Group, Inc., Lynchburg, VA (US)

( * ) Notice: Subject to any disclaimer, the term of this patent is extended or adjusted under 35 U.S.C. 154(b) by 525 days.

(21) Appl. No.: 13/774,439

(22) Filed: Feb. 22, 2013

(65) Prior Publication Data

US 2014/0131584 A1 May 15, 2014

Related U.S. Application Data

(60) Provisional application No. 61/727,060, filed on Nov. 15, 2012.

(51) Int. Cl.
*G01T 1/167* (2006.01)
*G01T 7/02* (2006.01)

(52) U.S. Cl.
CPC ............ *G01T 1/167* (2013.01); *G01T 7/02* (2013.01)

(58) Field of Classification Search
CPC ............ G01T 1/36; G01T 1/167; G01T 7/02
USPC ......................... 250/370.06, 336.1
See application file for complete search history.

(56) References Cited

U.S. PATENT DOCUMENTS

| 2,706,789 | A | * | 4/1955 | Hughes ........................ 378/53 |
| 3,500,446 | A | * | 3/1970 | Hasegawa et al. ........... 250/308 |
| 4,629,600 | A | * | 12/1986 | Ishiguro et al. .............. 376/257 |
| 5,250,806 | A | * | 10/1993 | Rhein-Knudsen et al. .. 250/254 |
| 5,614,721 | A | * | 3/1997 | Pandelisev .................... 250/368 |
| 2009/0027678 | A1 | * | 1/2009 | Salerno et al. ............... 356/440 |
| 2014/0021345 | A1 | * | 1/2014 | Maucec et al. ............... 250/260 |

* cited by examiner

*Primary Examiner* — David Porta
*Assistant Examiner* — Gisselle Gutierrez
(74) *Attorney, Agent, or Firm* — Nelson Mullins Riley & Scarborough, LLP

(57) ABSTRACT

The present invention relates generally to the field of gamma ray spectroscopy monitoring and a system for accomplishing same to monitor one or more aspects of various isotope production processes. In one embodiment, the present invention relates to a monitoring system, and method of utilizing same, for monitoring one or more aspects of an isotope production process where the monitoring system comprises: (A) at least one sample cell; (B) at least one measuring port; (C) at least one adjustable collimator device; (D) at least one shutter; and (E) at least one high resolution gamma ray spectrometer.

20 Claims, 2 Drawing Sheets

Comptom Compensating Detector
Gamma Rays Hit both NaI(Ti) and High Purity
Germanium (HPGe), NaI(Ti) signal utilized to
correct Comptom background HPGe

GAMMA RAY SPECTROSCOPY MONITORING METHOD AND APPARATUS

RELATED APPLICATION DATA

This patent application claims priority to U.S. Provisional Patent Application No. 61/727,060 filed Nov. 15, 2012 and titled "Gamma Ray Spectroscopy Monitoring Method and Apparatus." The complete text of this application is hereby incorporated by reference as though fully set forth herein in its entirety.

STATEMENT REGARDING FEDERAL RIGHTS

This invention was made with government support under U.S. Department of Energy Contract No. DE-FC52-09NA29596 awarded by the U.S. Department of Energy. The government has certain rights in the invention.

FIELD AND BACKGROUND OF THE INVENTION

1. Field of the Invention

The present invention relates generally to the field of gamma ray spectroscopy monitoring and a system for accomplishing same to monitor one or more aspects of various isotope production processes. In one embodiment, the present invention relates to a monitoring system, and method of utilizing same, for monitoring one or more aspects of an isotope production process where the monitoring system comprises: (A) at least one sample cell located inside a hot cell that is connected to a medical isotope reactor, or other type of nuclear reactor; (B) at least one measuring port located in and through the hot cell and/or a hot cell wall, the measuring port forming at least one gamma ray window through the hot cell and/or a hot cell wall, where the measuring port has an inner gamma ray transparent plug located at the internal end thereof and an outer gamma ray transparent plug located at the external end thereof; (C) at least one adjustable collimator device operably coupled to the at least one measuring port; (D) at least one shutter located outside of the hot cell and operatively coupled to the outer end of the measuring port; and (E) at least one high resolution gamma ray spectrometer that is operably coupled to the hot cell and positioned in such a manner that gamma rays from the hot cell are supplied to the at least one high resolution gamma ray spectrometer through at least one opening in the shutter that is transparent to gamma rays.

2. Description of the Related Art

Many radio-isotopes are prepared by irradiation of a uranium-235 ($^{235}$U) target or solution in a nuclear reactor and subsequent separation of the fission product isotopes of interest including, but not limited to, one or more of $^{99}$Mo, $^{137}$Ce, $^{131}$I, $^{89}$Sr, $^{133}$Xe $^{90}$Y, $^{99m}$Tc, and/or $^{99}$Tc by chemical means. These purifications are usually carried out in a shielded "hot cell" on solutions of the fission or irradiation products. This is true whether the solutions are the result of irradiation of solid $^{235}$U targets or the product of an aqueous homogeneous reactor (AHR) or other radioactive solutions. As is known to those of skill in the art, the purity of the final product of various medical radio-isotopes is subject to various regulatory requirements set forth by, for example, The U.S. Food and Drug Administration.

Given the regulations and requirements placed on various medical radio-isotopes, it is necessary to evaluate the purification process and product purity. Many of the intended products, like $^{99}$Mo, $^{137}$Ce, $^{131}$I, $^{89}$Sr, $^{133}$Xe $^{90}$Y, $^{99m}$Tc, and/or $^{99}$Tc and potential contaminants are gamma-emitting radioisotopes that can be measured by gamma-ray spectroscopy.

Ordinarily, such evaluation requires that an aliquot of the process sample be removed from the hot cell, diluted to a calibrated volume in a specified geometrical configuration and measured "off-line" on a gamma ray spectrometer. This is a time consuming process for product isotopes that have relatively short half-lives, like 66 hour $^{99}$Mo or 8 day $^{131}$I, and introduces the potential for exposure of the analyst to unnecessary radiation.

Accordingly, given the above, a need exists in the art for a system and method for effectively and safely measuring various properties of one or more samples of medical radio-isotopes without exposing testing personnel to undue radiation.

SUMMARY OF THE INVENTION

The present invention relates generally to the field of gamma ray spectroscopy monitoring and a system for accomplishing same to monitor one or more aspects of various isotope production processes. In one embodiment, the present invention relates to a monitoring system, and method of utilizing same, for monitoring one or more aspects of an isotope production process where the monitoring system comprises: (A) at least one sample cell located inside a hot cell that is connected to a medical isotope reactor, or other type of nuclear reactor; (B) at least one measuring port located in and through the hot cell and/or a hot cell wall, the measuring port forming at least one gamma ray window through the hot cell and/or a hot cell wall, where the measuring port has an inner gamma ray transparent plug located at the internal end thereof and an outer gamma ray transparent plug located at the external end thereof; (C) at least one adjustable collimator device operably coupled to the at least one measuring port; (D) at least one shutter located outside of the hot cell and operatively coupled to the outer end of the measuring port; and (E) at least one high resolution gamma ray spectrometer that is operably coupled to the hot cell and positioned in such a manner that gamma rays from the hot cell are supplied to the at least one high resolution gamma ray spectrometer through at least one opening in the shutter that is transparent to gamma rays.

Accordingly, one aspect of the present invention is drawn to a gamma ray spectroscopy monitoring system comprising: (i) at least one sample cell located inside a hot cell that is connected to a medical isotope reactor; (ii) at least one measuring port located in and through the hot cell and/or a hot cell wall, the measuring port forming at least one gamma ray window through the hot cell and/or a hot cell wall, where the measuring port has an inner gamma ray transparent plug located at the internal end thereof and an outer gamma ray transparent plug located at the external end thereof; (iii) at least one adjustable collimator device operably coupled to the at least one measuring port; (iv) at least one shutter located outside of the hot cell and operatively coupled to the outer end of the measuring port; and (v) at least one high resolution gamma ray spectrometer operably coupled to the hot cell and positioned in such a manner that gamma rays from the hot cell are supplied to the at least one high resolution gamma ray spectrometer through at least one opening in the shutter that is transparent to gamma rays.

In yet another aspect of the present invention, there is provided a gamma ray spectroscopy monitoring system comprising: (I) at least one sample cell located inside a hot cell that is connected to a nuclear reactor; (II) at least one measuring port located in and through the hot cell and/or a hot cell wall, the measuring port forming at least one gamma ray window through the hot cell and/or a hot cell wall, where the measuring port has an inner gamma ray transparent plug located at the internal end thereof and an outer gamma ray transparent plug located at the external end thereof; (III) at least one adjustable collimator device operably coupled to the at least one measuring port; (IV) at least one three-position shutter located outside of the hot cell and operatively coupled to the outer end of the measuring port; and (V) at least one high resolution gamma ray spectrometer operably coupled to the hot cell and positioned in such a manner that gamma rays from the hot cell are supplied to the at least one high resolution gamma ray spectrometer through at least one opening in the shutter that is transparent to gamma rays.

The various features of novelty which characterize the invention are pointed out with particularity in the claims annexed to and forming a part of this disclosure. For a better understanding of the invention, its operating advantages and specific benefits attained by its uses, reference is made to the accompanying drawings and descriptive matter in which exemplary embodiments of the invention are illustrated.

DESCRIPTION OF THE INVENTION

Figure 1:
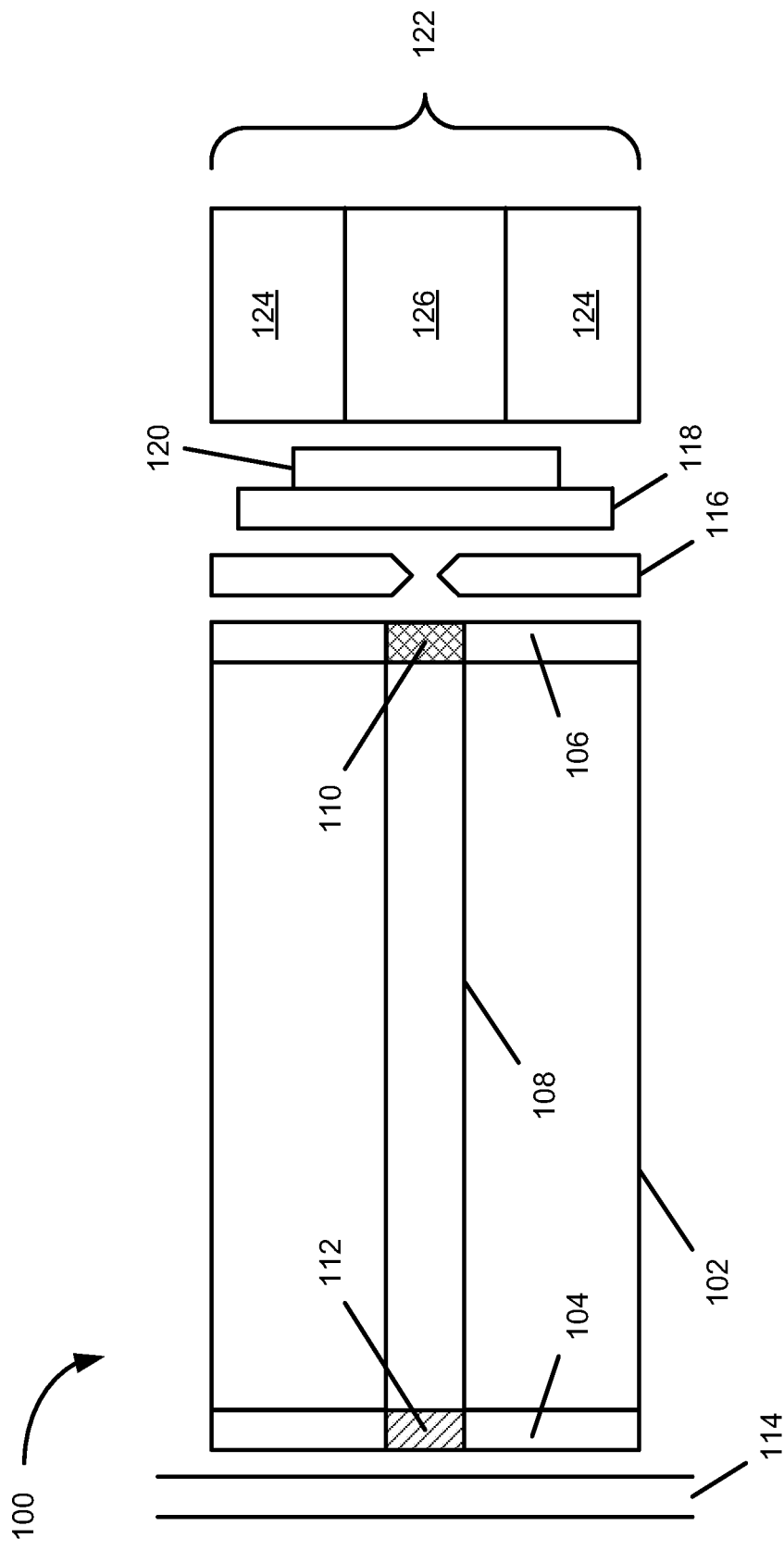
FIG. 1 is an illustration of one embodiment of a gamma ray spectroscopy system of the present invention.

The present invention relates generally to the field of gamma ray spectroscopy monitoring and a system for accomplishing same to monitor one or more aspects of various isotope production processes. In one embodiment, the present invention relates to a monitoring system, and method of utilizing same, for monitoring one or more aspects of an isotope production process where the monitoring system comprises: (A) at least one sample cell located inside a hot cell that is connected to a medical isotope reactor, or other type of nuclear reactor; (B) at least one measuring port located in and through the hot cell and/or a hot cell wall, the measuring port forming at least one gamma ray window through the hot cell and/or a hot cell wall, where the measuring port has an inner gamma ray transparent plug located at the internal end thereof and an outer gamma ray transparent plug located at the external end thereof; (C) at least one adjustable collimator device operably coupled to the at least one measuring port; (D) at least one shutter (e.g., a two-position shutter, a three-position shutter, or even a four or more-position shutter) located outside of the hot cell and operatively coupled to the outer end of the measuring port; and (E) at least one high resolution gamma ray spectrometer that is operably coupled to the hot cell and positioned in such a manner that gamma rays from the hot cell are supplied to the at least one high resolution gamma ray spectrometer through at least one opening that is transparent to gamma rays.

As used herein a "hot cell" refers to one or more shielded nuclear radiation containment chambers. As is known to those of skill in the art hot cells are used in both the nuclear-energy and the nuclear-medicines industries. They are required to protect various individuals from being exposed to radioactivity associated with and/or generated by one or more radioactive isotopes by providing a safe containment box in which such individuals can control and manipulate various equipment related to, for example, the production of one or more desired radio-isotopes.

In the nuclear industry, hot cells are used to inspect spent nuclear fuel rods and to work with other items which are high-intensity gamma ray emitters. For example, the processing of medical isotopes, having been irradiated in a nuclear reactor or particle accelerator, can be carried out in a hot cell. Various activities including, but not limited to, the cutting of used fuel, the dissolving of fuel, and/or the first extraction cycle of a nuclear reprocessing PUREX process (highly active cycle) are examples of processes that should be done in a hot cell.

Additionally, in the nuclear medicine industry, or during the production of medical radio-isotopes, one or more hot cells can be utilized for the preparation of various medically desirable radio-isotopes (e.g., $^{99}$Mo, $^{137}$Ce, $^{131}$I, $^{89}$Sr, $^{133}$Xe $^{90}$Y, $^{99m}$Tc, $^{99}$Tc, etc.).

Hot cells are commonly used in the nuclear medicine industry for the production of radiopharmaceuticals, for the manipulation and dispensing of radiopharmaceuticals (hospitals). A user must never be subject to shine paths that are emitted from the radioactive isotopes and therefore there generally is heavy shielding around the containment boxes, which can be made out of stainless steel (e.g., stainless alloys 316, 316L, 316LN, 316Ti, 304, 304L, 304LN, 304H, 347, etc.), or other materials such as polyvinyl chloride (PVC) or Corian™. This shielding can be ensured by the use of lead or materials such as concrete (large and/or thicker walls are required) or even tungsten. The amount of radioactivity present in the hot cell, the energy of the gamma photons emitted by the radioisotopes, and the number of neutrons that are formed by the material will prescribe how thick the shielding must be. For instance a 1 kCi source of $^{60}$Co will require thicker shielding than a 1 kCi source of $^{192}$Ir to give the same dose rate at the outer surface of the hot cell. Also, if some actinide materials such as spent nuclear fuel are used within the hot cell, then a layer of water or polyethylene may be needed to lower the neutron dose rate.

In order to view what is in the hot cell, cameras can be used but require replacement on a regular basis, or most commonly, lead glass is used. There are several densities for lead glass, but the most common is 5.2 g/cc. A rough calculation for lead equivalence would be to multiply the lead metal thickness by 2.5 (e.g., 10 mm of lead metal would require a 25 mm thick lead glass window). Older hot cells used $ZnBr_2$ solution in a glass tank to shield against high-energy gamma rays. This shielded the radiation without darkening the glass (as happens to leaded glass with exposure). This solution also "self-repairs" any damage caused by radiation interaction, but leads to optical distortion due to the difference in optical indices of the solution and glass. Tele-manipulators or tongs are used for the remote handling of equipment inside hot cells. These are incredibly valuable as they do not require the user to place his/her arms inside the containment box and be subject to heavy finger/hand doses. These need to be used in conjunction with a shielded sphere which can be made by most lead engineering companies.

Lead loaded gloves are often used in conjunction with tongs as they offer better dexterity and can be used in low radiation environments (such as hot cells used in hospital nuclear medicine labs). Some companies have developed tungsten loaded gloves which offer greater dexterity than lead loaded gloves, with better shielding than their counterparts. Gloves must be regularly replaced as the chemicals used for the cleaning/sterilization process of the containments cause considerable wear and tear. Hot cells are generally placed in clean rooms with an air classification ranging from D to B (C is the most common). It is extremely rare to find a hot cell which is placed in a class A or unclassified clean room.

Turning to the gamma ray spectroscopy monitoring system for the present invention, in one embodiment a system in accordance with the present invention comprises: (i) at least one sample cell located inside a hot cell that is connected to a medical isotope reactor, or other type of nuclear reactor; (ii) at least one measuring port located in and through the hot cell and/or a hot cell wall, the measuring port forming at least one gamma ray window through the hot cell and/or a hot cell wall, where the measuring port has an inner gamma ray transparent plug located at the internal end thereof and an outer gamma ray transparent plug located at the external end thereof; (iii) at least one adjustable collimator device operably coupled to the at least one measuring port; (iv) at least one shutter (e.g., a three-position shutter, etc.) located outside of the hot cell and operatively coupled to the outer end of the measuring port; and (v) at least one high resolution gamma ray spectrometer that is operably coupled to the hot cell and positioned in such a manner that gamma rays from the hot cell are supplied to the at least one high resolution gamma ray spectrometer through at least one opening that is transparent to gamma rays.

A more detailed explanation of the present invention will be explained with reference to FIG. 1. As is illustrated in FIG. 1, a gamma ray spectroscopy monitoring system 100 comprises a hot cell structure 102 (only a portion of which is illustrated in FIG. 1), the hot cell structure 102 having inner shielded wall 104 and outer shielded wall 106, a measuring port 108 that is located through, for example, the width of any suitable wall of hot cell 102 and through both the inner wall 104 and the outer wall 106, and a sample cell 114 of known dimensions through which a sample of the reactor process material can be directed via a series of suitable valves and other flow means. As would be apparent to those of skill in the art, sample cell 114 can be any suitable size so long as the dimensions thereof are known. Additionally, only a portion of sample cell 114 is illustrated in FIG. 1.

Figure 2:
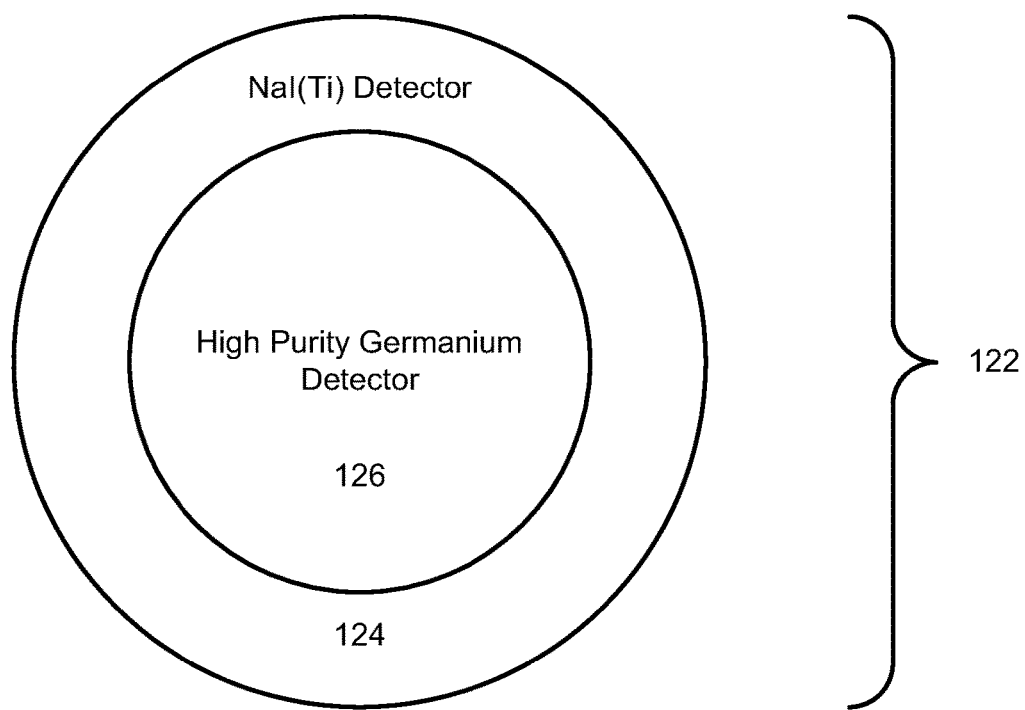
FIG. 2 is an end view of the Compton Compensating Detector that is part of the gamma ray spectroscopy system of FIG. 1.

As is further illustrated in FIG. 1, measuring port 108 has an inner gamma ray transparent plug 112 at the inner end of measuring port 108 and an outer gamma ray transparent plug 110 at the outer end of measuring port 108. System 100 further comprises a suitable collimator 116 (shown slightly open and represented by two portions in cross-section), a suitable shutter 118 (e.g., a three-position shutter), a mount 120 for a suitable point source gamma ray standard, and a Compton Compensating Detector 122 formed from a high purity germanium portion 126 that is surrounded by a NaI(Tl) (i.e., sodium iodide-thallium) or bismuth germanate portion 124. It should be noted that the present invention is not limited solely to the design of the Compton Compensating Detector disclosed herein. Rather, any suitable Compton Compensating Detector can be utilized in conjunction with the system of the present invention. Regarding FIG. 2, FIG. 2 is an end view of the Compton Compensating Detector 122 of FIG. 1.

The following is a description of a gamma ray spectroscopy system 100 of the present invention that can be used in radioactive environments such as the Medical Isotope Production System (MIPS) process stream or solutions from target dissolution or fuel processing. In one embodiment, system 100 of the present invention can be mounted on a process line to monitor product purity, process efficiency, and performance. As discussed above, the monitoring system 100 of the present invention comprises, among other items, sample cell 114 having known dimensions and composition, sample cell 114 being designed to contain the desired radioactive process fluid and wherein sample cell 114 is located within shielded hot cell 102. In one embodiment, sample cell 114 is part of the processing line, or a side-line, mounted to be viewed through measuring port 108 of hot cell 102 with the measuring spectrometer located outside of hot cell 102.

As noted above, system 100 comprises: (i) sample cell 114 (only a portion of which is illustrated in FIG. 1) having known dimensions and composition, through which the process stream may be directed by valves and which is located inside hot cell 102; (ii) measuring port 108 which is aligned with at least a portion of sample cell 114, comprising a tube or pipe passing through any suitable wall of hot cell 102 that is sealed at the inner end with a material 112 of high transparency to gamma rays (e.g., polymethyl methacrylate resin, a metal material, or a metal alloy material) and an outer gamma ray transparent plug 110 formed from any suitable material (e.g., polymethyl methacrylate resin, a metal material, or a metal alloy material); (iii) a gamma-ray opaque adjustable collimator 116 made of tungsten, lead or stainless steel operably coupled to measuring port 108, where the collimator 116 is, in one embodiment, adjustable to permit fine attenuation of the radiation from the sample cell that impinges detector 122; (iv) outside of hot cell 102 and positioned relative to measuring port 108 there is a three-position high density sliding shutter/shield 118 to provide open port, closed port, and closed port with a mixed gamma ray calibration source, with shutter 118 facing the detector; and (v) a Compton Compensating Detector 122. The following should be noted with regard to plugs 110 and 112. Regarding outer gamma ray transparent plug 110 this plug will hereinafter be referred to as outer transparent plug 110 but it is to be understood that the transparency referred to here is gamma ray transparency and not necessarily visual transparency. Additionally, regarding inner gamma ray transparent plug 112 this plug will hereinafter be referred to as inner transparent plug 112 but it is to be understood that the transparency referred to here is gamma ray transparency and not necessarily visual transparency. In one embodiment, plugs 110 and 112 serve to prevent the transport of volatile radioactive material out of the hot cell through port 108.

In one embodiment, measuring port 108 is filled with air or some suitable inert gas. Suitable inert gases include, but are not limited to, nitrogen, argon, helium, etc. Furthermore, it should be understood that a thin metal material for use of inner transparent plug 112 is preferable as it reduces the frequency and/or need to replace inner transparent plug 112 due to radiation damage suffered by inner transparent plug 112. In one embodiment, inner transparent plug 112 can be formed from a suitable alloy of stainless steel in the shape of a metal foil of a known thickness (e.g., in the range of about 1 micron to about 250 microns). The effect of stainless steel inner transparent plug 112 on the measurement system of the present invention can be calculated in order to enable system 100 of the present invention to make accurate measurements absent the attenuation effect on the gamma ray signal by inner transparent plug 112. Outer transparent plug 110 can, in one embodiment, be formed from a polymer (e.g., polymethyl methacrylate resin), a suitable metal, or suitable metal alloy. Again, if outer transparent plug 110 is formed from a metal, or metal alloy, composition then the attenuation effect on the gamma ray signal passing through measuring port 108 needs to be taken into account so as to accurately calibrate system 100 of the present invention. As is noted above, one of skill in the art would be readily able to calculate any attenuation effects present in system 100 due to the materials utilized to form inner transparent plug 112 and/or outer transparent plug 110 upon determining the compositional make-up and various dimensions of inner transparent plug 112 and/or outer transparent plug 110.

In another embodiment, inner transparent plug 112 and/or outer transparent plug 110 can each be independently formed from a suitable metal including, but not limited to, iron, beryllium, aluminum, tin, copper, nickel, titanium, or zirconium. In still another embodiment, inner transparent plug 112 and/or outer transparent plug 110 can each be independently formed from a suitable metal alloy including, but not limited to, steel, stainless steel, iron-containing alloys, beryllium-containing alloys, aluminum-containing alloys, tin-containing alloys, copper-containing alloys, nickel-containing alloys, titanium-containing alloys, zirconium-containing alloys, brass alloys, or bronze alloys. In one embodiment, when either one or both of inner transparent plug 112 and/or outer transparent plug 110 are formed from a metal, or metal alloy, material the thickness of each respective plug can independently range from about 1 micron to about 250 microns, or from about 2.5 microns to about 225 microns, or from about 5 microns to about 200 microns, or from about 7.5 microns to about 175 microns, or from about 10 microns to about 150 microns, or from about 12.5 microns to about 125 microns, or from about 15 microns to about 100 microns, or from about 17.5 microns to about 75 microns, or from about 20 microns to about 50 microns, or even from about 25 microns to about 40 microns. Here, as well as elsewhere in the specification and claims, individual numerical values and/or range limits can be combined to form new, additional, and/or undisclosed ranges.

In another embodiment, the thickness of the metal material, metal alloy material, or polymer material that is independently selected to form plugs 110 and 112 can be any thickness so long as their respective impact on the gamma ray transparency of the system of the present invention is either known or can be calculated. This is important in that it permits a system in accordance with the present invention to be properly calibrated. Additionally, although structures 110 and 112 of the present invention are referred to herein as "plugs," one of skill in the art would appreciate that at the various thickness disclosed herein such "plugs" might actually be more accurately referred to as a metal foil and/or sheet, metal alloy foil and/or sheet, or polymer sheet or film. Accordingly, the term "plug" is to be broadly construed and is not limited to its traditional meaning.

Given the above, it should be noted that the materials from which inner transparent plug 112 and outer transparent plug 110 are formed from can be a wide range of materials. Various considerations should be taken into account when choosing the material from which to make either inner transparent plug 112 and/or outer transparent plug 110. One non-limiting consideration to take into account is the attenuation effect the various materials utilized to form inner transparent plug 112 and/or outer transparent plug 110 will have on the gamma ray signal that is passing through measuring port 108. As explained above, those of skill in the art are able to determine such attenuation effects upon knowing the compositional make-up and dimensions of the material, or materials, that are utilized to form inner transparent plug 112 and/or outer transparent plug 110. Given this, a wide range of polymer materials, metals, and/or metal alloys can be utilized to form either one or both of inner transparent plug 112 and outer transparent plug 110.

Regarding collimator 116, collimator 116 is adjustable so as to permit attenuation of a gamma-ray signal from the sample cell 114 by covering at least a portion of the measuring port 108. Collimator 116 can be operated manually with, for example, a screw mechanism or remotely by means of a drive motor (e.g., a pulse drive motor). In one embodiment, after being calibrated collimator 116 of system 100 can be locked in place. The gamma-ray process-line standard source is, in one embodiment, prepared from a mix of long-lived multi-line gamma emitters (such as $^{60}$Co and $^{152}$Eu) and is contained in a tube of the same composition and geometry as the process-line sample cell. This provides a means to correct for attenuation by transparent plugs 110 and 112 and correct for the length of measuring port 108. Regarding shutter 118, shutter 118 can also be operated manually or by a drive motor. This provides the means to calibrate the detector and perform quality checks independent of the process line source. In one embodiment, the open port portion of shutter 118 has an adjustable high density metal shim to permit additional collimation of the sample radiation beam from the sample port, if that is necessary.

In one embodiment, in order to calibrate system 100 for any attenuation effects present due to, at a minimum, inner transparent plug 112 and outer transparent plug 110, an in-cell gamma ray standard can be placed in a reproducible position beside sample cell 114 so as to aid in and/or facilitate the calibration of system 100. This is one means by which system 100 can be calibrated in order to account for any attenuation effects caused by the design parameters of system 100 on a gamma ray signal passing through measuring port 108.

Regarding Compton Compensating Detector 122, this device is located adjacent to, near, or in line with shutter 118. The use of such a spectrometer provides greater sensitivity for radioisotopes that have lower abundance of gamma rays in the presence of a high total activity level. As is known to those of skill in the art, there are several types of Compton Compensating Detectors available. As such, the present invention is not limited to just the type illustrated in FIG. 2. As is illustrated in FIG. 2, one type consists of a high resolution semiconductor gamma ray spectrometer, such as a high purity germanium crystal (HPGe) surrounded by a large secondary detector crystal (guard detector), such as NaI(Tl) (i.e., sodium iodide-thallium) or bismuth germanate. Another type consists of a segmented high purity germanium crystal detector. Either type uses anticoincidence circuitry to differentiate against spurious counts due to the Compton Effect, thus providing greater sensitivity for lower abundance gamma rays of the intended products or contaminants. The desired analytical range is in one embodiment from about 50 keV to about 1900 keV to cover the anticipated range of both the target isotopes and potential contaminant isotopes.

In one instance, system 100 of the present invention is advantageous in that is permits unique coupling of a Compton Compensating Detector to the window of a shielded hot cell. Given this set-up, there is a reduction in the time to obtain spectral data on process performance, maintains sample integrity, and eliminates analyst radiation exposure from sample handling.

As a non-limiting example, sample cell 114 can be a tube having an inner diameter of 3.54 mm and can, in one instance, be formed of suitable material such as stainless steel (e.g., stainless alloys 316, 316L, 316LN, 316Ti, 304, 304L, 304LN, 304H, 347, etc.). This keeps the high activity sample to be measured inside the cell and reduces the problem of the time required to remove such a high activity, short-lived sample from the hot cell and puts it in a known measurement geometry. The volume of the cell is that of a right circular cylinder whose volume is defined by its diameter and the length exposed through measuring port 108. In one non-limiting instance, measuring port 108 can have an inner diameter of 2.54 cm and a length equal to that of the thickness of a wall of hot cell 102 (e.g., 60 cm). Transparent plug 112 should be replaceable in the event that it suffers unacceptable radiation damage. Measuring port 108 collimates the sample radiation and its diameter, in combination with the sample cell dimensions, defines the sample volume. This solves the problem of accessing the sample for measurement.

While not wishing to be bound to any one or more distinct advantages, system 100 of the present invention is advantageous in that: (a) the sample is never removed from the hot cell, maintaining sample integrity and identity; (b) the time to obtain a measurement made is reduced (this is vital for short-lived products); (c) analyst exposure is eliminated; (d) the measured sample is maintained as a part of the process stream, reducing product loss; (e) the detector can be energy and efficiency-calibrated in place, and quality control measurements can be made more efficiently; (f) the sample radiation beam can be collimated and attenuated in a controlled and reproducible manner; and (g) corrections for attenuation by the transparent plug and sample-to-detector distance can be made in place. This is especially important when transparent plug 112 needs to be replaced.

One alternative to system 100 of the present invention is to remove aliquots of the sample stream from the hot cell through an access port for sample preparation in a suitable "hot" laboratory and measurement on a gamma ray spectrometer in a conventional counting room. This necessarily delays obtaining results due to the time required for such transfers and also introduces the potential for personnel exposure and sample decay.

While specific embodiments of the present invention have been shown and described in detail to illustrate the application and principles of the invention, it will be understood that it is not intended that the present invention be limited thereto and that the invention may be embodied otherwise without departing from such principles. In some embodiments of the invention, certain features of the invention may sometimes be used to advantage without a corresponding use of the other features. Accordingly, all such changes and embodiments properly fall within the scope of the following claims.

What is claimed is:

1. A gamma ray spectroscopy monitoring system comprising:
    (i) at least one sample cell located inside a hot cell that is connected to a medical isotope reactor;
    (ii) at least one measuring port located in and through the hot cell and/or a hot cell wall, the measuring port forming at least one gamma ray window through the hot cell and/or a hot cell wall, where the measuring port has an inner gamma ray transparent plug located at the internal end thereof and an outer gamma ray transparent plug located at the external end thereof, wherein the inner and outer gamma ray transparent plugs serve to prevent the transport of volatile radioactive material out of the hot cell through the at least one measuring port;
    (iii) at least one adjustable collimator device operably coupled to the at least one measuring port;
    (iv) at least one shutter located outside of the hot cell and operatively coupled to the outer end of the measuring port; and
    (v) at least one high resolution gamma ray spectrometer operably coupled to the hot cell and positioned in such a manner that gamma rays from the hot cell are supplied to the at least one high resolution gamma ray spectrometer through at least one opening in the shutter that is transparent to gamma rays.

2. The gamma ray spectroscopy monitoring system of claim 1, wherein the outer transparent plug is formed from a polymethyl methacrylate resin.

3. The gamma ray spectroscopy monitoring system of claim 1, wherein either one or both of the inner and/or outer transparent plug are formed from a metal or metal alloy material.

4. The gamma ray spectroscopy monitoring system of claim 1, wherein the at least one adjustable collimator device is formed of tungsten, a tungsten-containing alloy, lead, or a lead-containing alloy.

5. The gamma ray spectroscopy monitoring system of claim 1, wherein the at least one shutter is a three-position shutter and is formed of tungsten, a tungsten-containing alloy, lead, or a lead-containing alloy.

6. The gamma ray spectroscopy monitoring system of claim 1, wherein the at least one high resolution gamma ray spectrometer is a Compton Compensating Detector formed from a combination of high purity germanium crystal (HPGe) surrounded by a large secondary detector crystal.

7. The gamma ray spectroscopy monitoring system of claim 1, wherein the inner gamma ray transparent plug and the outer gamma ray transparent plug are each independently formed from a metal selected from iron, beryllium, aluminum, tin, copper, nickel, titanium, or zirconium.

8. The gamma ray spectroscopy monitoring system of claim 1, wherein the inner gamma ray transparent plug and the outer gamma ray transparent plug are each independently formed from a metal alloy selected from steel, stainless steel, iron-containing alloys, beryllium-containing alloys, aluminum-containing alloys, tin-containing alloys, copper-containing alloys, nickel-containing alloys, titanium-containing alloys, zirconium-containing alloys, brass alloys, or bronze alloys.

9. The gamma ray spectroscopy monitoring system of claim 1, wherein the inner gamma ray transparent plug and the outer gamma ray transparent plug are each independently formed from a metal foil, metal alloy foil, or polymer material having a thickness in the range of about 1 micron to about 250 microns.

10. The gamma ray spectroscopy monitoring system of claim 1, wherein the inner gamma ray transparent plug and the outer gamma ray transparent plug are each independently formed from a metal foil, metal alloy foil, or polymer material having a thickness in the range of about 2.5 micron to about 225 microns.

11. A gamma ray spectroscopy monitoring system comprising:
    (I) at least one sample cell located inside a hot cell that is connected to a nuclear reactor;
    (II) at least one measuring port located in and through the hot cell and/or a hot cell wall, the measuring port forming at least one gamma ray window through the hot cell and/or a hot cell wall, where the measuring port has an inner gamma ray transparent plug located at the internal end thereof and an outer gamma ray transparent plug located at the external end thereof, wherein the inner and outer gamma ray transparent plugs serve to prevent the transport of volatile radioactive material out of the hot cell through the at least one measuring port;

(III) at least one adjustable collimator device operably coupled to the at least one measuring port;

(IV) at least one three-position shutter located outside of the hot cell and operatively coupled to the outer end of the measuring port; and (V) at least one high resolution gamma ray spectrometer operably coupled to the hot cell and positioned in such a manner that gamma rays from the hot cell are supplied to the at least one high resolution gamma ray spectrometer through at least one opening in the shutter that is transparent to gamma rays.

12. The gamma ray spectroscopy monitoring system of claim 11, wherein the outer transparent plug is formed from a polymethyl methacrylate resin.

13. The gamma ray spectroscopy monitoring system of claim 11, wherein either one or both of the inner and/or outer transparent plug are formed from a metal or metal alloy material.

14. The gamma ray spectroscopy monitoring system of claim 11, wherein the at least one adjustable collimator device is formed of tungsten, a tungsten-containing alloy, lead, or a lead-containing alloy.

15. The gamma ray spectroscopy monitoring system of claim 11, wherein the at least one three-position shutter is formed of tungsten, a tungsten-containing alloy, lead, or a lead-containing alloy.

16. The gamma ray spectroscopy monitoring system of claim 11, wherein the at least one high resolution gamma ray spectrometer is a Compton Compensating Detector formed from a combination of high purity germanium crystal (HPGe) surrounded by a large secondary detector crystal.

17. The gamma ray spectroscopy monitoring system of claim 11, wherein the inner gamma ray transparent plug and the outer gamma ray transparent plug are each independently formed from a metal selected from iron, beryllium, aluminum, tin, copper, nickel, titanium, or zirconium.

18. The gamma ray spectroscopy monitoring system of claim 11, wherein the inner gamma ray transparent plug and the outer gamma ray transparent plug are each independently formed from a metal alloy selected from steel, stainless steel, iron-containing alloys, beryllium-containing alloys, aluminum-containing alloys, tin-containing alloys, copper-containing alloys, nickel-containing alloys, titanium-containing alloys, zirconium-containing alloys, brass alloys, or bronze alloys.

19. The gamma ray spectroscopy monitoring system of claim 11, wherein the inner gamma ray transparent plug and the outer gamma ray transparent plug are each independently formed from a metal foil, metal alloy foil, or polymer material having a thickness in the range of about 1 micron to about 250 microns.

20. The gamma ray spectroscopy monitoring system of claim 11, wherein the inner gamma ray transparent plug and the outer gamma ray transparent plug are each independently formed from a metal foil, metal alloy foil, or polymer material having a thickness in the range of about 2.5 micron to about 225 microns.

* * * * *